(12) United States Patent
Isaacson et al.

(10) Patent No.: US 12,251,528 B2
(45) Date of Patent: Mar. 18, 2025

(54) CANNULA WITH LIGHT-EMITTING OPTICAL FIBER

(71) Applicant: Becton, Dickinson and Company, Franklin Lakes, NJ (US)

(72) Inventors: S. Ray Isaacson, Layton, UT (US); Ralph L. Sonderegger, Farmington, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1085 days.

(21) Appl. No.: 17/071,776

(22) Filed: Oct. 15, 2020

(65) Prior Publication Data

US 2021/0023345 A1 Jan. 28, 2021

Related U.S. Application Data

(63) Continuation of application No. 15/461,354, filed on Mar. 16, 2017, now Pat. No. 10,835,718.

(Continued)

(51) Int. Cl.
*A61M 25/09* (2006.01)
*A61B 5/00* (2006.01)
(Continued)

(52) U.S. Cl.
CPC ........... *A61M 25/09* (2013.01); *A61B 5/0059* (2013.01); *A61B 5/15* (2013.01); *A61B 5/15003* (2013.01);
(Continued)

(58) Field of Classification Search
CPC .. A61M 25/09; A61M 25/0067; A61M 25/06; A61M 25/0606; A61M 2025/0166;
(Continued)

(56) References Cited

U.S. PATENT DOCUMENTS

| 3,789,841 A | 2/1974 | Antoshkiw |
| 4,317,445 A | 3/1982 | Robinson |

(Continued)

FOREIGN PATENT DOCUMENTS

| CN | 1184677 | 6/1998 |
| CN | 1997312 | 7/2007 |

(Continued)

OTHER PUBLICATIONS

Schneider et al: "The Fibre Fabry Perot sensor. A long-term manometry sensor for quantitative intraluminal pressure measurement of the gastrointestinal tract", Clinical Physics and Physiological Measurement, Institute of Physics Publishing, Bristol, GB, vol. 11, No. 4, Nov. 1, 1990, pp. 319-325.

*Primary Examiner* — Jason E Flick
(74) *Attorney, Agent, or Firm* — Kirton McConkie; Whitney Blair; Kevin Stinger

(57) ABSTRACT

A catheter device to visually identify a blood vessel may include a cannula. The cannula may include a distal tip, an elongated tubular shaft, and an inner lumen formed by the elongated tubular shaft. The cannula may also include an optical fiber, which may be disposed within the inner lumen of the cannula. The optical fiber may include a distal end and a proximal end. The optical fiber may be configured to emit light from the distal end.

7 Claims, 3 Drawing Sheets

Related U.S. Application Data

(60) Provisional application No. 62/314,258, filed on Mar. 28, 2016.

(51) Int. Cl.

| | | |
|---|---|---|
| *A61B 5/15* | (2006.01) | |
| *A61B 5/153* | (2006.01) | |
| *A61M 25/00* | (2006.01) | |
| *A61M 25/01* | (2006.01) | |
| *A61M 25/06* | (2006.01) | |

(52) U.S. Cl.
CPC .............. *A61B 5/153* (2013.01); *A61B 5/489* (2013.01); *A61M 25/0067* (2013.01); *A61M 25/06* (2013.01); *A61M 25/0606* (2013.01); *A61M 2025/0166* (2013.01); *A61M 2205/583* (2013.01)

(58) Field of Classification Search
CPC ........ A61M 2205/583; A61M 25/0043; A61M 25/0105; A61M 2205/587; A61M 2210/12; A61M 25/01; A61M 2205/58; A61B 5/0059; A61B 5/489; A61B 5/0082; A61B 5/0084; A61B 5/4887

See application file for complete search history.

(56) References Cited

U.S. PATENT DOCUMENTS

| | | | |
|---|---|---|---|
| 4,682,895 A | 7/1987 | Costello | |
| 4,800,886 A | 1/1989 | Nestor | |
| 5,054,882 A | 10/1991 | Riccitelli et al. | |
| 5,092,845 A | 3/1992 | Chang | |
| 5,124,130 A | 6/1992 | Costello et al. | |
| 5,271,398 A | 12/1993 | Schlain et al. | |
| 5,452,076 A | 9/1995 | Schopper et al. | |
| 5,460,182 A | 10/1995 | Goodman et al. | |
| 5,772,636 A | 6/1998 | Brimhall et al. | |
| 5,779,680 A | 7/1998 | Yoon | |
| 7,496,392 B2 | 2/2009 | Alarcon et al. | |
| 7,787,923 B2 | 8/2010 | Alarcon et al. | |
| 8,597,252 B2 | 12/2013 | Burkholz et al. | |
| 8,954,134 B2* | 2/2015 | Imam | A61B 90/39 |
| | | | 600/476 |
| 9,267,906 B2 | 2/2016 | Anway et al. | |
| 9,339,221 B1 | 5/2016 | Heaton et al. | |
| 9,700,697 B2 | 7/2017 | Gasparyan et al. | |
| 9,737,213 B1 | 8/2017 | Heaton, II et al. | |
| 10,850,046 B2 | 12/2020 | Isaacson et al. | |
| 2004/0127853 A1 | 7/2004 | Howell | |
| 2006/0167405 A1 | 7/2006 | Kint et al. | |
| 2006/0184048 A1 | 8/2006 | Saadat | |
| 2006/0264745 A1 | 11/2006 | Da Silva | |
| 2007/0016130 A1 | 1/2007 | Leeflang et al. | |
| 2007/0293748 A1 | 12/2007 | Engvall et al. | |
| 2008/0009751 A1 | 1/2008 | Berndt | |
| 2008/0243031 A1 | 10/2008 | Seibel et al. | |
| 2008/0249487 A1 | 10/2008 | Engvall | |
| 2008/0262359 A1 | 10/2008 | Tearney et al. | |
| 2010/0081873 A1 | 4/2010 | Tanimura et al. | |
| 2010/0317964 A1 | 12/2010 | Hendriks et al. | |
| 2011/0009772 A1 | 1/2011 | Braun et al. | |
| 2011/0077477 A1 | 3/2011 | Romey et al. | |
| 2011/0255828 A1 | 10/2011 | Sudarshanam | |
| 2012/0088991 A1 | 4/2012 | Nachabe et al. | |
| 2012/0215065 A1 | 8/2012 | Mukherjee | |
| 2014/0276024 A1 | 9/2014 | Stigall et al. | |
| 2015/0196271 A1 | 7/2015 | Nair | |
| 2015/0305603 A1 | 10/2015 | Gal et al. | |
| 2015/0314105 A1* | 11/2015 | Gasparyan | A61M 5/427 |
| | | | 604/117 |
| 2017/0274184 A1 | 9/2017 | Isaacson et al. | |
| 2017/0281287 A1 | 10/2017 | Au | |

FOREIGN PATENT DOCUMENTS

| | | |
|---|---|---|
| CN | 101959470 | 1/2011 |
| CN | 102458229 | 5/2012 |
| CN | 102929070 | 2/2013 |
| CN | 103347461 | 10/2013 |
| EP | 2710974 | 3/2014 |
| JP | H05506949 | 10/1993 |
| JP | H0829207 | 2/1996 |
| JP | H08131549 | 5/1996 |
| JP | 2010523197 | 7/2010 |
| JP | 2012529332 | 11/2012 |
| JP | 2013009949 | 1/2013 |
| JP | 2013502269 | 1/2013 |
| JP | 2013542773 | 11/2013 |
| JP | 2015083140 | 4/2015 |
| KR | 20180135257 | 12/2018 |
| WO | 86/03832 | 7/1986 |
| WO | 2006/001759 | 1/2006 |
| WO | 2009/123026 | 10/2009 |
| WO | 2012/101583 | 8/2012 |
| WO | 2012/101584 | 8/2012 |
| WO | 2015/056257 | 4/2015 |
| WO | 2015/168655 | 11/2015 |
| WO | 2015/200712 | 12/2015 |

* cited by examiner

CANNULA WITH LIGHT-EMITTING OPTICAL FIBER

RELATED APPLICATIONS

This application is a continuation of U.S. patent application Ser. No. 15/461,354, filed on Mar. 16, 2017, and entitled CANNULA WITH LIGHT-EMITTING OPTICAL FIBER, which claims the benefit of U.S. Provisional Patent Application No. 62/314,258, filed on Mar. 28, 2016, and entitled CANNULA WITH LIGHT-EMITTING OPTICAL FIBER, which is incorporated herein in its entirety.

BACKGROUND OF THE INVENTION

Placing a cannula in a desired destination of a body of a patient may be a difficult task for a clinician in the medical field. For example, it may be difficult to place the cannula in proper position in a blood vessel, such as a vein, for infusion and/or blood collection. It may also be difficult to place the cannula in proper position in a spinal canal for infusion and/or cerebrospinal fluid collection. The clinician may want to advance the cannula far enough to access the blood or cerebrospinal fluid but may not want to advance the cannula too far so as to injure a wall of the vein, the spinal cord, or the spinal cord dura. Thus, it is important for the clinician to know when the cannula is positioned within the vein or spinal canal.

To assist in positioning the cannula in the vein to be accessed, clinicians have traditionally used a number of techniques. These include use of a tourniquet, palpitation, rubbing the area, asking the patient to make a fist, and others. In some instances, to assist in positioning the cannula of a catheter device in the vein, the clinician may confirm that there is "flashback" of blood into, for example, a flashback chamber associated with the catheter device. Flashback generally entails an appearance of a small amount of blood within the catheter device, which may be visible to the clinician.

Once proper placement of the cannula into the blood vessel is confirmed via flashback, the clinician may apply pressure to the blood vessel by pressing down on the patient's skin over the blood vessel, distal to the cannula. The finger pressure may momentarily occlude the vessel, minimizing further blood flow through the cannula and the catheter device. The clinician may then withdraw the cannula from the catheter device. Flashback of blood into the flashback chamber may occur when the cannula is properly placed within the blood vessel but may be irreversible. Thus, the clinician may not be able to detect when he or she has transfixed the vein. Further, flashback of blood into the flashback chamber may not be instantaneous and may take some time.

Accordingly, there is a need in the art for devices, systems, and methods that provide a continuous and/or instantaneous indication of a location of the distal tip of the cannula. Such devices, systems, and methods are disclosed herein.

BRIEF SUMMARY OF THE INVENTION

The present disclosure relates generally to a cannula that includes a light-emitting optical fiber. In particular, the present disclosure relates to devices, systems, and associated methods to visually identify a blood vessel of a patient using a catheter device having the cannula that includes the light-emitting optical fiber. In some embodiments, the cannula of the catheter device may include a distal tip, an elongated tubular shaft, and an inner lumen formed by the elongated tubular shaft. In some embodiments, the optical fiber may be at least partially disposed within the inner lumen of the cannula. In some embodiments, the optical fiber may include a distal end and a proximal end. In some embodiments, the optical fiber may be configured to emit light from the distal end and/or one or more notch features each defining a discontinuity in the optical fiber. Each of the discontinuities may include a localized deviation of optical fiber loss. In some embodiments, one or more of the discontinuities may include a break or notch formed in an outer surface of the optical fiber. The discontinuities may be formed in any suitable manner that increases an amount of light that escapes from the optical fiber. For example, the discontinuities may be formed by sandblasting, laser etching, etc. In some embodiments, one or more of the discontinuities may include a slight chemical etching which may break the surface of the optical fiber, increasing an amount of light that escapes the optical fiber. In some embodiments, one or more of the discontinuities may be formed by a surface finish, which may be rough and/or microscopic. In some embodiments, one or more of the discontinuities may be visible. In some embodiments, in order to increase an amount of light that is emitted from the optical fiber, a number of discontinuities in a particular optical fiber may be increased and/or one or more particular types of discontinuities, such as, for example, larger, visible discontinuities, may be selected. In some embodiments, the cannula may include more than one optical fiber.

In some embodiments, the distal end of the optical fiber may be disposed at least proximate the distal tip of the cannula. Thus, in some embodiments, the cannula may be configured to light up or illuminate at least proximate the distal tip. In some embodiments, a high intensity light source may be coupled with the optical fiber and may produce the light, which may be transmitted along the optical fiber and emitted from the optical fiber. The light emitted from the optical fiber may be referred to in the present disclosure as "emitted light." In some embodiments, the high-intensity light source may include a lamp, such as, for example, an arc lamp, a quartz halogen lamp, or any other type of high-intensity lamp. In some embodiments, the high-intensity light source may include a laser, a high-intensity light-emitting diode (LED), or another high-intensity light source.

The emitted light may include one or more wavelengths of light. In some embodiments, the emitted light may not include one or more particular wavelengths of light. For example, the emitted light may not include the particular wavelengths corresponding to a color of blood or red, and when the emitted light shines on the blood within the blood vessel, the blood may not reflect the emitted light. For example, the emitted light may not include red light having a light emission peak in wavelengths of 640 to 680 nanometers. In some embodiments, the emitted light, which may not include red light, may include one or more other particular wavelengths of light, which may correspond to a color of tissue and/or skin of the patient. The other particular wavelengths of light may be reflected by tissue and/or skin of the patient. Thus, when the distal tip of the cannula is inserted in the patient, the tissue and/or the skin may be illuminated and may reflect the emitted light, but when the distal tip of the cannula reaches the blood vessel, the blood in the blood vessel may not reflect the emitted light. In some embodiments, in response to the blood not reflecting the emitted light, when the distal tip of the cannula is positioned within the blood vessel, the clinician may observe darkness as opposed to light at a location of the blood vessel. A change from light to the darkness as the cannula moves from the skin and/or the tissue to within the blood vessel may provide a visual cue to the clinician that the distal tip of the cannula is positioned within the blood vessel.

As another example, in some embodiments, the emitted light may not include one or more wavelengths of light corresponding to a color of the tissue and/or the skin. In these embodiments, the emitted light may include red light, corresponding to the color of blood. As the distal tip of the cannula is being inserted in the patient, the tissue and/or the skin may reflect the emitted light at a reduced level compared to the blood or not at all. The blood in the blood vessel may reflect the emitted light and may be illuminated when the emitted light is shined on the blood. The illumination of the blood may indicate the distal tip of the cannula is positioned within the blood vessel. The illumination of the blood in the blood vessel may facilitate an increase in an intensity of light seen by the clinician and reflected from anatomy of the patient (blood vessel, tissue, skin, etc.). For example, the clinician may see a reduced intensity of light or no light reflected from the tissue and/or the skin as the cannula is advanced, and then in response to the cannula reaching the blood of the blood vessel, the increase in the intensity of light may occur as the blood vessel is illuminated.

In some embodiments, when the optical fiber illuminates the blood in the blood vessel, the blood vessel may act as a light pipe and the emitted light may be distributed throughout a length of the blood vessel, which may signal to the clinician that the cannula is positioned within the blood vessel. In some embodiments, when the optical fiber illuminates the blood in the blood vessel, the blood vessel may be seen through the skin of the patient, providing a visual cue to the clinician as to a position of the distal tip of the cannula. Similarly, when the optical fiber illuminates the tissue of the patient, the tissue may be seen through the skin of the patient, providing a visual cue to the clinician as to the position of the distal tip of the cannula.

In some embodiments, the cannula may include an opening in the elongated shaft. In some embodiments, the opening may be disposed towards the distal tip of the cannula. In these and other embodiments, the optical fiber may include one or more grooves, each of which may extend from the distal end of the optical fiber to a portion of the optical fiber aligned with the opening. In some embodiments, the one or more grooves may be configured to allow blood to flow between the distal tip and the opening. In some embodiments, multiple grooves in the optical fiber may allow the optical fiber to rotate while maintaining alignment between one particular groove and the opening. In some embodiments, the blood may then flow out of the opening and into a portion of the catheter device, such as a catheter adapter, for example, where the blood can be seen by the clinician, which may signal to the clinician that the cannula is positioned within the blood vessel.

Once the blood flows out of the opening, the signal to the clinician may not be reversible. Thus, the clinician may unknowingly insert the cannula too far into the blood vessel, transfixing the blood vessel. Advantageously, in some embodiments, the optical fiber may allow continuous monitoring of the position of the cannula. In some embodiments, the optical fiber may indicate the cannula has been inserted too far into the blood vessel and has transfixed the blood vessel. For example, in response to the emitted light including red light and not including a particular wavelength corresponding to a color of the tissue, the blood in the blood vessel may be illuminated when the emitted light is shined on the blood. However, if transfixing of the blood vessel occurs, less light than reflected by the blood or no light may be reflected by tissue of the blood vessel wall or tissue outside of the blood vessel wall, and the clinician may perceive darkness as opposed to light at a location of the tissue.

As another example, in response to the emitted light not including red light and instead including another color of light corresponding to tissue or other colors of light corresponding to the tissue, when the cannula is positioned within the blood vessel, the blood vessel may not reflect light and the clinician may perceive darkness as opposed to light at a location of the blood vessel. However, in response to transfixing the blood vessel and inserting the blood vessel in the tissue, the tissue may illuminate, reflecting the emitted light, and the clinician may observe the illuminated tissue through the skin of the patient.

In some embodiments, the opening may be eliminated, which may reduce manufacturing costs of the cannula. However, in some embodiments, the cannula may include both the opening and the optical fiber, allowing dual mechanisms to detect entry of the distal tip of the cannula into the blood vessel.

In some embodiments, the optical fiber may be fixed within the cannula, and the optical fiber and the cannula may move together in the proximal and/or the distal direction. For example, the optical fiber and the cannula may be configured in an interference fit. In some embodiments, the optical fiber may not move beyond the distal tip of the cannula. In some embodiments, a length of the optical fiber may prevent the optical fiber from moving beyond the distal tip of the cannula.

In some embodiments, the optical fiber may act similar to a guidewire. For example, the optical fiber may be configured to move past the distal tip of the cannula to guide a catheter into the blood vessel of the patient. In some embodiments, the catheter may follow the optical fiber into the blood vessel to reduce trauma to the blood vessel during advancement of the catheter into the blood vessel. In some embodiments, the optical fiber may not only reduce trauma to the blood vessel by guiding the catheter into the blood vessel, but may emit high-intensity light to illuminate the blood vessel, allowing the clinician to more clearly see a location of the blood vessel, which may aid in advancement of the catheter. The illuminated blood vessel may act as a light pipe and the emitted light may be distributed throughout a length of the blood vessel.

In some embodiments, the optical fiber may be configured to emit light from one or more notch features of the optical fiber, each of the notch features defining a discontinuity in the optical fiber. In some embodiments, one or more of the notch features of the optical fiber may be disposed in the distal end of the optical fiber and/or proximate the distal end of the optical fiber. In some embodiments, the notch features of the optical fiber may be exposed when the optical fiber moves past the distal tip of the cannula. In these and other embodiments, the distal end of the optical fiber may be rounded and/or smooth, which may allow the optical fiber to enter the blood vessel more smoothly and/or without puncturing the blood vessel. The rounded distal end of the optical fiber may also make it more difficult for the optical fiber to transfix the blood vessel.

In some embodiments, when the cannula is inserted in the patient, the distal end of a particular optical fiber may be configured to move past the distal tip may be disposed within and/or at least proximate the distal tip of the cannula, allowing the position of the cannula to be determined, as previously described. In some embodiments, in response to the cannula being positioned within the blood vessel, the particular optical fiber may be advanced past the distal tip of the cannula to guide the catheter into the blood vessel. A wavelength of the emitted light from the particular optical fiber may be tuned, in any of the ways previously described, to monitor and/or determine a position of the distal end of the particular optical fiber prior to and/or after advancement of the particular optical fiber past the distal tip of the cannula. For example, the emitted light from the particular optical fiber may not include one or more wavelengths of light corresponding to a color of the tissue and/or the skin. For example, the emitted light from the particular optical fiber may include red light, corresponding to the color of blood. The illumination of the blood in the blood vessel may indicate the distal end of the particular optical fiber is disposed within the blood vessel.

The catheter device may include any catheter device. Example catheter devices may include both straight and ported catheters such as the AUTOGUARD™ shielded catheter commercially available from Becton, Dickinson, and Company, integrated and non-integrated peripheral intravenous catheters, winged needle sets, blood collection sets, an IV access set such as the BD NEXIVA™ Closed Intravenous (IV) Catheter system available from Becton, Dickinson, and Company, etc. In some embodiments, the optical fiber may extend through the catheter device from a proximal end of the catheter device to a distal end of the device or through a portion of the catheter device. In some embodiments, the optical fiber may exit the proximal end of the catheter device and be coupled with the high-intensity light source.

In some embodiments, a proximal end of the optical fiber may be uncoupled from the high-intensity light source and disposed of after use. In some embodiments, the optical fiber may be disposed of with a catheter adapter of the catheter device, for example. In some embodiments, an optical connector may selectively couple the optical fiber to the high-intensity light source. In some embodiments, the optical connector may be disposed in any number of positions. For example, the optical connector may be disposed at a proximal end of the catheter device. Although a single optical fiber may be referred to throughout the present disclosure, it is understood that the catheter device may include multiple optical fibers, which may be disposed within the cannula. For example, multiple optical fibers may emit light and/or be used to guide the catheter.

In some embodiments, a method of assisting introduction of the catheter into the blood vessel of the patient may include inserting the cannula into the blood vessel. The method may also include advancing the optical fiber beyond the distal tip of the cannula such that a portion of the optical fiber is disposed outside the cannula and another portion of the optical fiber is disposed within the cannula. The method may include guiding the catheter along the portion of the optical fiber and into the blood vessel. The method may also include withdrawing the cannula from the catheter, which may be performed after the catheter is positioned within the blood vessel.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the cannula locator device, cannula locator system, and associated methods, as represented in FIGS. 1 through 5, is not intended to limit the scope of the invention, as claimed, but is merely representative of some embodiments of the invention.

Generally, this application relates to a cannula that includes a light-emitting optical fiber. In particular, the present disclosure relates to devices, systems, and associated methods to visually locate a blood vessel of a patient using a catheter device, which may include the cannula and the light-emitting optical fiber.

Figure 1:
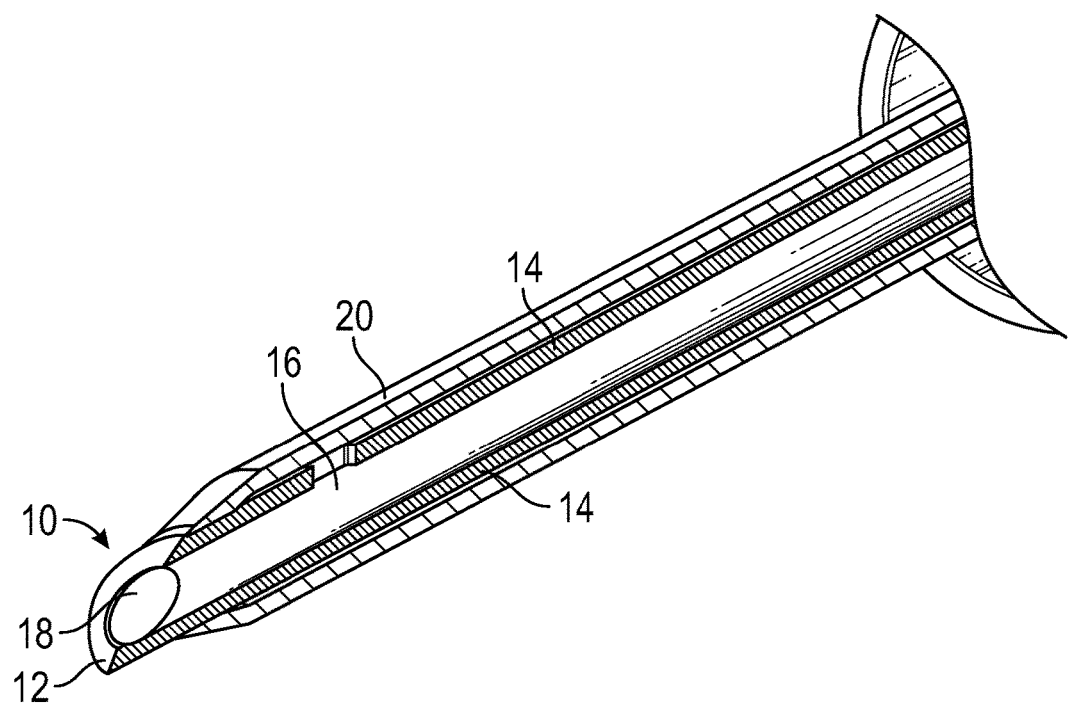
FIG. 1 is a cut-away side view of an example optical fiber disposed within an example cannula, according to some embodiments.

Referring now to FIG. 1, in some embodiments, the cannula 10 may include a distal tip 12, an elongated tubular shaft 14, and an inner lumen formed by the elongated tubular shaft 14. In some embodiments, an optical fiber 16 may be at least partially disposed within the inner lumen of the cannula. In some embodiments, the optical fiber 16 may include a distal end 18 and a proximal end (not illustrated in FIG. 1). In some embodiments, the optical fiber 16 may be configured to emit light from the distal end 18 and/or one or more notch features (not illustrated in FIG. 1) defining discontinuities in the optical fiber 16. In some embodiments, the notch features may be disposed at least proximate the distal end 18. In some embodiments, the cannula 10 may include multiple optical fibers 16. In some embodiments, the multiple optical fibers 16 may be aligned parallel to each other in the inner lumen of the cannula 10. In some embodiments, the multiple optical fibers 16 may be twisted or braided together, which may increase a strength of the multiple optical fibers 16.

In some embodiments, the distal end 18 of the optical fiber 16 may be disposed at least proximate the distal tip 18 of the cannula 10, as illustrated in FIG. 1. Thus, in some embodiments, the cannula 10 may be configured to light up or illuminate at least proximate the distal tip 18. In some embodiments, a high intensity light source may be coupled with the proximal end of the optical fiber 16 and may produce the emitted light, which may be transmitted along the optical fiber 16 and emitted from the optical fiber 16.

The emitted light may include one or more wavelengths of light. In some embodiments, the emitted light may not include one or more particular wavelengths of light. For example, the emitted light may not include the particular wavelengths corresponding to a color of blood or red, and when the emitted light shines on the blood within the blood vessel, the blood may not reflect the emitted light.

For example, the emitted light may not include red light having a light emission peak in wavelengths of 640 to 680 nanometers. In some embodiments, the emitted light, which may not include red light, may include one or more other particular wavelengths of light, which may correspond to a color of tissue and/or skin of the patient. The other particular wavelengths of light may be reflected by tissue and/or skin of the patient. Thus, when the distal tip 12 of the cannula 10 is inserted in the patient, the tissue and/or the skin may be illuminated and may reflect the emitted light, but when the distal tip 12 of the cannula 10 reaches the blood vessel, the blood in the blood vessel may not reflect the emitted light. In some embodiments, in response to the blood not reflecting the emitted light, when the distal tip 12 of the cannula 10 is positioned within the blood vessel, the clinician may observe darkness as opposed to light at a location of the blood vessel. A change from light to the darkness as the cannula 10 moves from the skin and/or the tissue to within the blood vessel may provide a visual cue to the clinician that the distal tip 12 of the cannula 10 is positioned within the blood vessel. In some embodiments, a distal end of the catheter may be disposed proximate the distal tip. Thus, the position of the distal tip of the cannula 10 may approximate a position of the catheter 20 through which the cannula 10 may extend.

As another example, in some embodiments, the emitted light may not include one or more wavelengths of light corresponding to a color of the tissue and/or the skin. In these embodiments, the emitted light may include red light, corresponding to the color of blood. As the distal tip 12 of the cannula 10 is being inserted in the patient, the tissue and/or the skin may reflect the emitted light at a reduced level compared to the blood or not at all. The blood in the blood vessel may reflect the emitted light and may be illuminated when the emitted light is shined on the blood. The illumination of the blood may indicate the distal tip 12 of the cannula 10 is positioned within the blood vessel. The illumination of the blood in the blood vessel may facilitate an increase in an intensity of light seen by the clinician and reflected from anatomy of the patient (blood vessel, tissue, skin, etc.). For example, the clinician may see a reduced intensity of light or no light reflected from the tissue and/or the skin as the cannula 10 is advanced, and then in response to the cannula 10 reaching the blood of the blood vessel, the increase in the intensity of light may occur as the blood vessel is illuminated.

In some embodiments, when the optical fiber 16 illuminates the blood in the blood vessel, the blood vessel may act as a light pipe and the emitted light may be distributed throughout a length of the blood vessel, which may signal to the clinician that the cannula 10 is positioned within the blood vessel. In some embodiments, when the optical fiber 16 illuminates the blood in the blood vessel, the blood vessel may be seen through the skin of the patient, providing a visual cue to the clinician as to a position of the distal tip 12 of the cannula 10. Similarly, when the optical fiber 16 illuminates the tissue of the patient, the tissue may be seen through the skin of the patient, providing a visual cue to the clinician as to the position of the distal tip 12 of the cannula 10.

Figure 2:
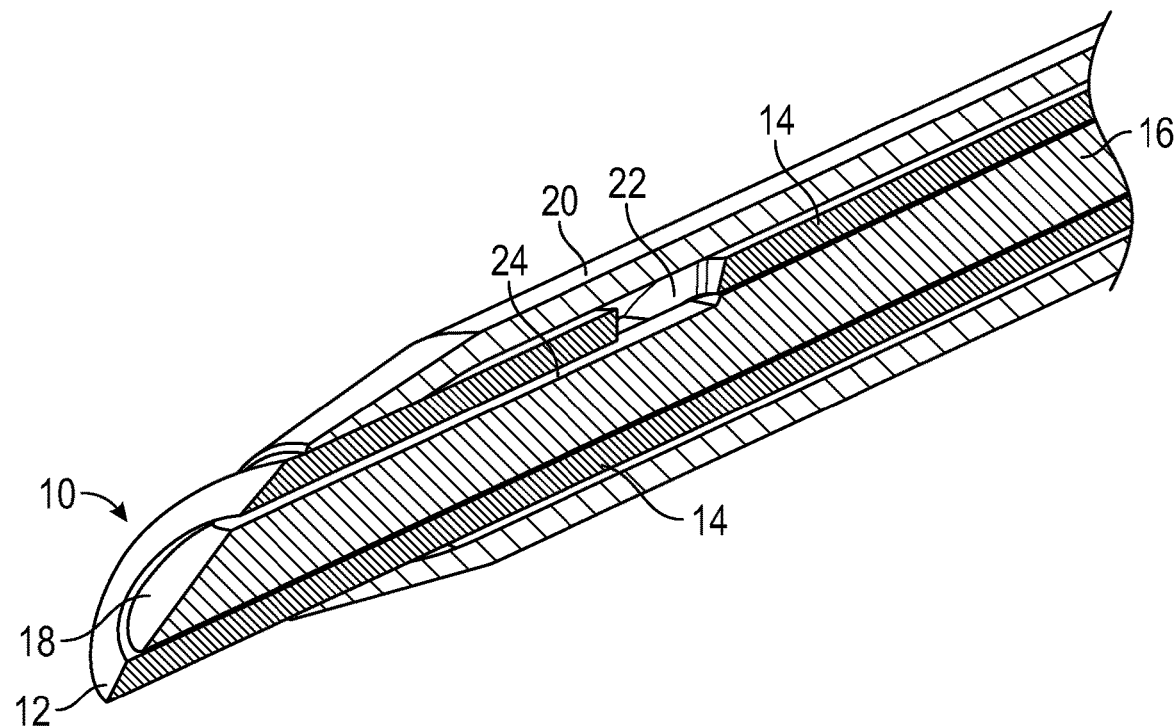
FIG. 2 is a cross-sectional view of the optical fiber disposed within the cannula, illustrating a groove in the optical fiber, according to some embodiments.

Referring now to FIG. 2, in some embodiments, the cannula may include an opening 22 in the elongated shaft 14. In some embodiments, the opening 22 may be disposed towards the distal tip 12 of the cannula 10. In these and other embodiments, the optical fiber 16 may include one or more grooves 24, which may extend from the distal end 18 of the optical fiber 16 to a portion of the optical fiber 16 aligned with the opening 22. In some embodiments, a particular groove 24 may be configured to allow blood to flow between the distal tip 12 and the opening 22. In some embodiments, the blood may then flow out of the opening 22 and into a portion of the catheter device, such as the catheter 20 and/or a catheter adapter, for example, where the blood can be seen by the clinician, which may signal to the clinician that the cannula 10 is positioned within the blood vessel.

Typically, once the blood flows out of the opening 22, the signal to the clinician may be irreversible. Thus, the clinician may unknowingly insert the cannula 10 too far into the blood vessel, transfixing the blood vessel. Advantageously, in some embodiments, the optical fiber 16 may allow continuous monitoring of the position of the cannula 10. In some embodiments, the optical fiber 16 may indicate the cannula 10 has been inserted too far into the blood vessel and has transfixed the blood vessel. For example, in response to the emitted light including red light and not including a particular wavelength corresponding to a color of the tissue, the blood in the blood vessel may be illuminated when the emitted light is shined on the blood. However, if transfixing of the blood vessel occurs, less light than reflected by the blood or no light may be reflected by tissue of the blood vessel wall or tissue outside of the blood vessel wall, and the clinician may perceive darkness as opposed to light at a location of the tissue.

As another example, in response to the emitted light not including red light and instead including another color of light corresponding to tissue or other colors of light corresponding to the tissue, when the cannula 10 is positioned within the blood vessel, the blood vessel may not reflect light and the clinician may perceive darkness as opposed to light at a location of the blood vessel. However, in response to transfixing the blood vessel and inserting the blood vessel in the tissue, the tissue may illuminate, reflecting the emitted light, and the clinician may observe the illuminated tissue through the skin of the patient.

In some embodiments, the opening 22 of the cannula 10 may be eliminated, which may reduce manufacturing costs of the cannula 10. However, in some embodiments, the cannula 10 may include both the opening 22 and the optical fiber 16, allowing dual mechanisms to detect entry of the distal tip 12 of the cannula 10 into the blood vessel.

In some embodiments, the optical fiber 16 may not move distally or proximally with respect to the cannula 10, and the optical fiber 16 and the cannula 10 may move together in the proximal and/or the distal direction. For example, the optical fiber 16 and the cannula 10 may be configured in an interference fit. In some embodiments, the optical fiber 16 may not move beyond the distal tip 12 of the cannula 10. In some embodiments, a length of the optical fiber 16 may prevent the optical fiber 16 from moving beyond the distal tip 12 of the cannula 10.

Figure 3:
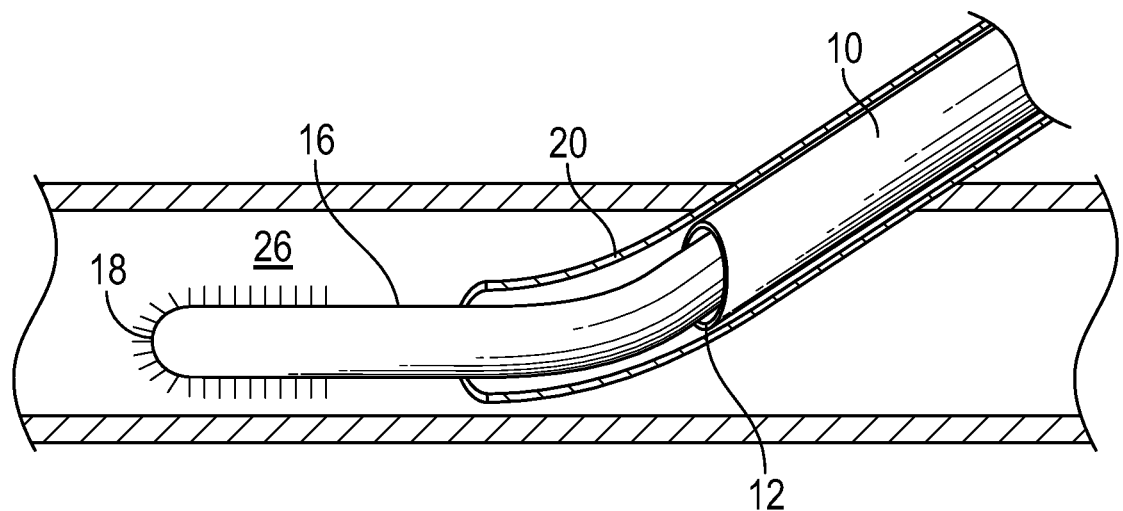
FIG. 3 is a perspective view of the optical fiber advanced beyond a distal tip of the cannula, according to some embodiments.

Referring now to FIG. 3, in some embodiments, the optical fiber 16 may act similar to a guidewire. For example, the optical fiber 16 may be configured to move past the distal tip 12 of the cannula 10 to guide a catheter 20 into the blood vessel 26 of the patient. In some embodiments, the catheter 20 may follow the optical fiber 16 into the blood vessel 26 to reduce trauma to the blood vessel 26 during advancement of the catheter 20 into the blood vessel 26. In some embodiments, the optical fiber 16 may not only reduce trauma to the blood vessel 26 by guiding the catheter 20 into the blood vessel 26, but may emit high-intensity light to illuminate the blood vessel 26, allowing the clinician to more clearly see a location of the blood vessel 26, which may aid in advancement of the catheter 20. In some embodiments, the high-intensity light may be emitted from the distal end 18 and/or one or more other discontinuities in the optical fiber 16. The discontinuities may be disposed along an upper and/or lower surface of the optical fiber 16, as illustrated in FIG. 3. The discontinuities may be exposed when the optical fiber 16 moves past the distal tip 12 of the cannula 10. The illuminated blood vessel 26 may act as a light pipe and the emitted light may be distributed throughout a length of the blood vessel 26.

Figure 4:
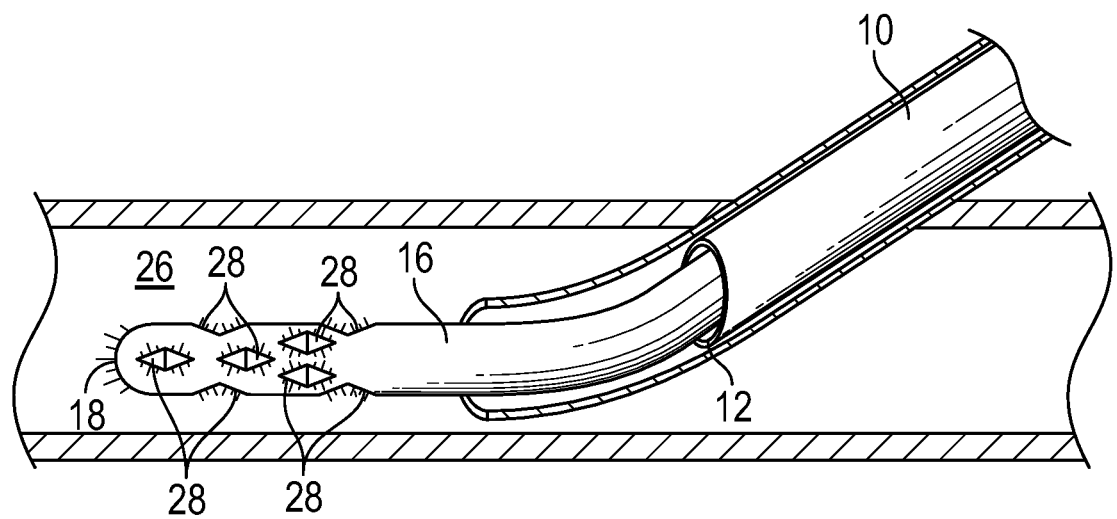
FIG. 4 is a perspective view of the optical fiber having one or more example notch features, according to some embodiments.

Referring now to FIG. 4, in some embodiments, the optical fiber 16 may be configured to emit light from one or more notch features 28 of the optical fiber 16, each of the notch features 28 defining a discontinuity in the optical fiber 16. In some embodiments, one or more of the notch features 28 of the optical fiber may be disposed towards the distal end 18 of the optical fiber. In some embodiments, the notch features 28 of the optical fiber 16 may be exposed when the optical fiber 16 moves past the distal tip 12 of the cannula 10. In these and other embodiments, the distal end 18 of the optical fiber may be rounded and/or smooth, which may allow the optical fiber 16 to enter the blood vessel 26 more smoothly and/or without puncturing the blood vessel 26. The rounded distal end 18 of the optical fiber 16 may also make it more difficult for the optical fiber 16 to transfix the blood vessel 26.

The notch features 28 of the optical fiber 16 may have various configurations and arrangements. The notch features 28 may provide multiple locations for light to be emitted from the optical fiber 16.

In some embodiments, when the cannula 10 is inserted in the patient, the distal end 18 of a particular optical fiber 16 may be configured to move past the distal tip 12 may be disposed within and/or at least proximate the distal tip 12 of the cannula 10, allowing the position of the cannula 10 to be determined, as previously described. In some embodiments, in response to the cannula 10 being positioned within the blood vessel 26, the particular optical fiber 16 may be advanced past the distal tip 12 of the cannula 10 to guide the catheter 20 into the blood vessel 26. A wavelength of the emitted light from the particular optical fiber may be tuned, in any of the ways previously described, to monitor and/or determine a position of the distal end 18 of the particular optical fiber 16 prior to and/or after advancement of the particular optical fiber 16 past the distal tip 12 of the cannula 10.

Figure 5:
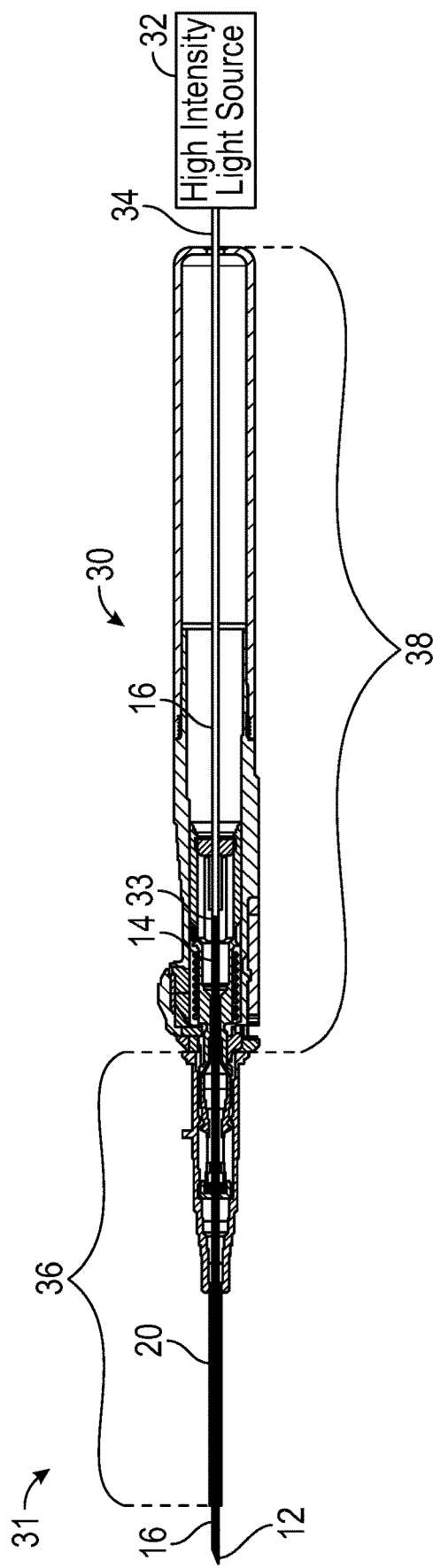
FIG. 5 is a cross-sectional view of the optical fiber extending through an example catheter device in a catheter system, according to some embodiments.

Referring now to FIG. 5, the catheter device 30 may include any catheter device. A system 31 may include the catheter device 30 and a high-intensity light source 32. Examples of catheter devices may include both straight and ported catheters such as the AUTOGUARD™ shielded catheter commercially available from Becton, Dickinson, and Company, integrated and non-integrated peripheral intravenous catheters, winged needle sets, blood collection sets, an IV access set such as the BD NEXIVA™ Closed Intravenous (IV) Catheter system available from Becton, Dickinson, and Company, etc. In some embodiments, the optical fiber 16 may extend through the catheter device 30 from a proximal end of the catheter device 30 to a distal end of the device or through a portion of the catheter device 30. In some embodiments, the optical fiber 16 may extend from at least proximate the distal tip, beyond a proximal end 33 of the cannula, and/or through an opening in the proximal end of the catheter device 30. In some embodiments, the optical fiber 16 may exit the proximal end of the catheter device and be coupled with the high-intensity light source 32.

In some embodiments, the cannula 10 may include a hypodermic needle such as, for example, an introducer needle. Further, the cannula 10 may be used in any suitable manner. For example, the cannula may be used during various medical procedures, such as, for example, an intravenous infusion, peripheral nerve block, blood draw, spinal tap, spinal anesthesia, or epidural. In these and other embodiments, the cannula 10 may be used with or without the catheter device 30.

In some embodiments, the high-intensity light source 32 may include a lamp, such as, for example, an arc lamp, a quartz halogen lamp, or any other type of high-intensity lamp. In some embodiments, the high-intensity light source may include a laser, a high-intensity light-emitting diode (LED), or another high-intensity light source.

In some embodiments, a proximal end 34 of the optical fiber 16 may be uncoupled from the high-intensity light source 32 and disposed of after use. In some embodiments, the optical fiber 16 may be disposed of with a catheter adapter 36 and/or a needle hub 38 of the catheter device 30, for example. In some embodiments, an optical connector (not illustrated in FIG. 5) may selectively couple the proximal end 34 of the optical fiber 16 to the high-intensity light source. In some embodiments, the optical connector may be disposed in any number of positions. For example, the optical connector may be disposed at a proximal end of the catheter device 30. Although a single optical fiber may be referred to throughout the present disclosure, it is understood that the catheter device 30 may include multiple optical fibers, which may be disposed within the cannula 10. For example, multiple optical fibers 16 may emit light and/or may be used to guide the catheter 20.

Figure 6:
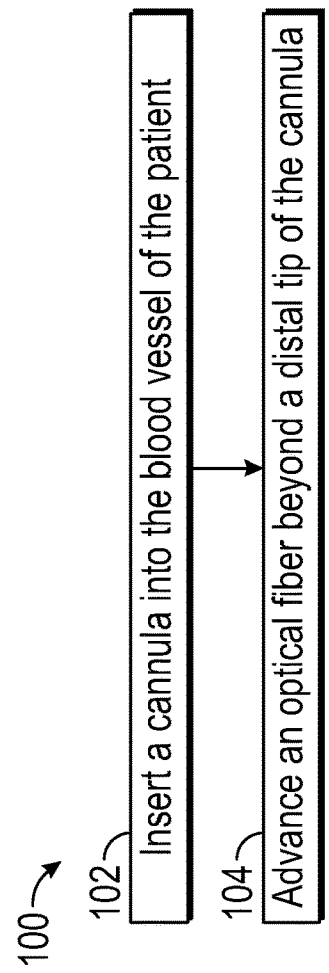
FIG. 6 is a flow chart of an example method of assisting introduction of the catheter into a blood vessel of a patient.

Referring now to FIG. 6, in some embodiments, a method 100 of assisting introduction of the catheter 20 into the blood vessel 26 of the patient may begin at block 102. At block 102, the cannula 10 may be inserted into the blood vessel 26. Block 102 may be followed by block 104. At block 104, the optical fiber 16 may be advanced beyond the distal tip 12 of the cannula 10 such that a portion of the optical fiber 16 is disposed outside the cannula 10 and another portion of the optical fiber 16 is disposed within the cannula 10.

Although illustrated as discrete blocks, various blocks may be divided into additional blocks, combined into fewer blocks, or eliminated, depending on the desired implementation. In some embodiments, the method 100 may include additional blocks. For example, the method 100 may include guiding the catheter 20 along the portion of the optical fiber 16 and into the blood vessel 26. As another example, the method 100 may include withdrawing the cannula 10 from the catheter, which may be performed after the catheter is positioned within the blood vessel. As a further example, the method 100 may include tuning a wavelength of light emitted from the optical fiber 16 to detect a position of the cannula 10 and/or the optical fiber 16 advanced beyond the distal tip 12.

In addition to the previously described embodiments of the optical fiber 16, the optical fiber 16 may be modified in any suitable manner that allows it to fulfill its intended purpose. Further, the cannula 10 and optical fiber 16 may be used in any suitable manner. For example, the cannula 10 and optical fiber 16 may allow a clinician to appropriately position the distal tip 12 of the cannula 10 during various medical procedures, such as, for example, an intravenous infusion, blood draw, spinal tap, or epidural. In some embodiments, the wavelength of the light may be tuned based on a color of a medium at a destination of the distal tip 12.

Also, in addition to the previously described embodiments of the system 31, the system 31 may be modified in any suitable manner that allows it to fulfill its intended purpose. Further, in addition to the previously described embodiments of the catheter device 30, the catheter device 30 may be modified in any suitable manner that allows it to fulfill its intended purpose.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method of assisting introduction of a single-lumen catheter into a blood vessel of a patient, comprising:

obtaining a cannula that is disposed within a single-lumen catheter, wherein the cannula comprises a distal tip, an elongated tubular shaft, and an inner lumen formed by the elongated tubular shaft, the distal tip of the cannula extending beyond a distal end of the single-lumen catheter, and wherein an optical fiber is positioned within the inner lumen of the cannula, the optical fiber having a rounded distal end that is positioned adjacent but proximal to the distal tip of the cannula, wherein the optical fiber is configured to emit light through discontinuities in the rounded distal end and through discontinuities positioned around a circumference of the optical fiber;

while the cannula remains disposed within the single-lumen catheter and the rounded distal end of the optical fiber remains adjacent but proximal to the distal tip of the cannula, inserting the cannula into the blood vessel of the patient, wherein the optical fiber illuminates the distal tip of the cannula as the cannula is inserted;

while the cannula remains disposed within the single-lumen catheter, advancing the optical fiber distally within the inner lumen of the cannula to cause the rounded distal end of the optical fiber including at least some of the discontinuities positioned around the circumference of the optical fiber to extend beyond the distal tip of the cannula to thereby illuminate the blood vessel; and after advancing the optical fiber distally within the cannula to cause the rounded distal end of the optical fiber including at least some of the discontinuities positioned around the circumference of the optical fiber to extend beyond the distal tip of the cannula, advancing the single-lumen catheter distally relative to the cannula and along the optical fiber to guide the catheter into the blood vessel.

2. The method of claim 1, further comprising activating a light source coupled to the optical fiber to produce the light.

3. The method of claim 2, wherein the light does not include red light having a light emission peak in wavelengths of 640 to 680 nanometers.

4. The method of claim 2, wherein the light is red light.

5. The method of claim 1, wherein the optical fiber is configured to cause an increased intensity of light to be visible as the distal tip of the cannula passes into the blood vessel.

6. The method of claim 1, wherein the optical fiber is configured to cause a decreased intensity of light to be visible as the distal tip of the cannula passes into the blood vessel.

7. The method of claim 1, wherein the elongated tubular shaft of the cannula includes a lateral opening, and wherein the optical fiber includes one or more grooves, each of the one or more grooves extending from the distal end of the optical fiber to a portion of the optical fiber aligned with the lateral opening, wherein each of the one or more grooves is configured to allow blood to flow between the distal tip and the lateral opening.

* * * * *